United States Patent [19]
Faccioli et al.

[11] Patent Number: 5,688,271
[45] Date of Patent: Nov. 18, 1997

[54] ORTHOPAEDIC DEVICE, ESPECIALLY FOR THE GRADUAL CORRECTION OF FRACTURES

[75] Inventors: Giovanni Faccioli, Monzambano; Daniele Venturini, Veronese; Guilio Zampieri, Torinese, all of Italy

[73] Assignee: Orthofix S.r.l., Bussolengo, Italy

[21] Appl. No.: 551,627

[22] Filed: Nov. 1, 1995

[51] Int. Cl.$^6$ ................................................. A61B 17/60
[52] U.S. Cl. .................................. 606/54; 606/57; 606/86
[58] Field of Search .................................. 606/54, 57, 86

[56] References Cited

U.S. PATENT DOCUMENTS 4,488,542  12/1984  Helland .
4,600,000  7/1986  Edwards .................................. 606/54
4,628,922  12/1986  Dewar .

*Primary Examiner*—Michael Buiz
*Assistant Examiner*—Daphja Shai
*Attorney, Agent, or Firm*—Hopgood, Calimafde, Kalil & Judlowe

[57] ABSTRACT

A device for the gradual correction of a bone fracture which has already been set in the operating theatre comprises an elongated structure (1) which defines a longitudinal axis (L) which can be positioned parallel to the bone and comprises a pair of end supports (10, 11) releasably anchored to corresponding bolt-bearing end clamps (6, 7) of an external fixation unit (2) which has already been fitted to the fractured pieces (F1, F2), a central body (24) connected to supports (10, 11) by connection means formed by longitudinal (32) and transverse (25) adjustment means to correct the longitudinal distance and transverse offset between the supports respectively, angular adjustment means (39) to correct the relative inclination of one of the supports with respect to the longitudinal axis (L) rotating it about a transverse axis (T), and centering means (40, 49, 50, 51) to align the transverse axis (T) with the centre of the fracture. The transverse axis (T) is perpendicular to the plane of action of the longitudinal (32) and transverse (25) adjustment means.

15 Claims, 5 Drawing Sheets

ORTHOPAEDIC DEVICE, ESPECIALLY FOR THE GRADUAL CORRECTION OF FRACTURES

FIELD OF APPLICATION

This invention relates to an orthopaedic device, especially for the gradual external correction of fractures which have already been set in the operating theatre.

The technique of stabilising fractures without having resort to conventional orthopaedic plasters and using so-called external fixation units has been known for many years. These devices generally comprise a series of bone bolts, generally in groups of two, which are temporarily fitted into the fractured pieces so that their ends project from the external surface of the patient's limb, these ends being anchored to a rigid frame provided with directionally adjustable clamps and joints.

When operating, after having cut through the soft tissues, the surgeon drills into the pieces of bone, implants the bolts and connects them to the corresponding clamps on the fixation unit, then lines up the edges of the fracture with the help of a brilliance amplifier. Once the fracture has been set, the surgeon immobilises the directionally-adjustable joints of the clamps in order to hold the pieces of bone in predetermined positions so as to line up the bony tissue correctly and cure the fracture.

After this operation the fracture must remain immobilised for a certain length of time to allow a bony callus to form between the pieces, which progressively unites the surfaces of the fracture until continuity is restored.

Experience has shown that moderate and early motive action of the limb encourages regrowth of the fracture and accelerates recovery by the limb, with consequent benefits for hospitalisation times and costs, and the patient's activity.

However, during motive action the pieces of the fracture may be subjected to slight displacements from their initial conditions, specially during the stage immediately following setting in the operating theatre, when the bony callus is still in the plastic state and is therefore readily subject to deformation. It is also possible that setting in the operating theatre may not have been performed perfectly, with the consequence of causing misalignment in the limb, imperfect regrowth at the margins and vascular problems in the vicinity of the fracture.

It would be useful to be able to correct these defects without having to resort to another operation, on a simple out-patient basis, avoiding the use of a local or full anaesthetic, merely with the help of a brilliance amplifier.

U.S. Pat. No. 4,628,922 (University College, London) discloses means for the external setting of fractures comprising two clamps which can be anchored into groups of bolts inserted into the respective stumps of the fracture, these clamps being in turn attached to a rigid elongatable rod. Each clamp has means for rotating the corresponding group of bolts about three axes at right angles to each other which intersect at a single point located within the bone. During an operation the device is fitted to the clamps to effect setting, and is then removed after the fixation unit has been anchored to the clamps. When the pieces of the fracture are rotated about the centres of rotation of the clamps appreciable translational movements can occur, and these must be compensated for by elongating the rod.

U.S. Pat. No. 4,488,542 (Helland) discloses a device for the correction of fractures which also provides a pair of end clamps mounted on an elongatable bar of polygonal cross-section by means of supports which can be orientated in two planes at right angles to each other. Each support comprises a first part which is integral with the bar and a second part which is integral with the clamp. The first part has the shape of a guide curve with a radius of curvature corresponding approximately to the distance between the clamp and the axis of the bone and with teeth provided on the outer edge of the guide. The second part comprises an endless screw which engages the teeth on the guide curve of the first part and can rotate about an axis substantially perpendicular to the plane in which the guide lies. One of the clamps can also rotate through a few degrees with respect to its corresponding support along a longitudinal axis parallel to that of the bar in order to compensate for slight twisting of the fracture pieces about a longitudinal axis.

In some known fixation units, such as e.g. the one manufactured and marketed by the Italian firm CITIEFFE, under the name ST.A.R 90 (Registered Trademark), the bolt-bearing clamps are mounted on a pair of rods which can move laterally in a transverse and longitudinal direction with respect to a central rigid body, in which these translational movements can be effected on the micrometer scale by means of suitable adjustment devices.

These known means are suitable for setting fractures even after they have been operated on in an operating theatre, and may also be used to apply compression, tension, rotational and in some cases also torsional forces to the pieces of fractured bone.

However, in these known devices the means which are used to effect rotation and torsion of the pieces of bone also give rise to undesired transverse and longitudinal movements with respect to the centre of the fracture. These movements affect the muscular tissues and the surrounding nerve ends making full or at least local anaesthesia necessary.

Finally, known external fixation units do not permit action on other devices but must remain stablly inserted into the limb until it is completely cured.

DESCRIPTION OF THE INVENTION

The principal object of this invention is to eliminate the abovementioned disadvantages by means of an orthopaedic device for gradual correction on an out-patient basis in order to correct random or accidental positioning errors present in a fracture which has already been set in the operating theatre.

A particular object within the scope of this principal object mentioned above is to provide means for the reliable accurate micrometric correction of fractures in the longitudinal, transverse, angular and torsional directions, which acts on the components of an external fixation unit which has already been implanted onto the fractured pieces themselves.

A further particular object is to provide a device capable of assisting the correction of fractures in patients on an outpatient basis reducing the use of X-rays to a minimum.

These objects are accomplished by an orthopaedic device, in particular for the gradual external correction of fractures which have already been set in the operating theatre, comprising an elongated structure defining a longitudinal axis which can be positioned parallel to the limb in which the said structure has a pair of end supports which are releasably anchored to corresponding bolt-holding clamps of an external fixation unit which has already been implanted on the pieces of a fracture, a central body attached to the said supports by means of adjustable connections which comprises longitudinal adjustment means to correct the longitudinal distance between the said supports, transverse adjustment means to correct the transverse offset between the said supports, angular adjustment means to correct the relative inclination of at least one of the said supports with respect to the said longitudinal axis by means of rotation about a transverse axis, and centering means to align the said transverse axis with the centre of the fracture, in which the said transverse axis is perpendicular to the plane of action of the said longitudinal and transverse adjustment means. Using a device of the type indicated above it is possible to effect correction in one plane by acting directly on the clamps of the axial fixation unit in a predetermined plane. The correction in that plane is not affected by subsequent corrections in different planes, thus reducing the time for which the fracture is handled and exposure to X-rays. With the patient's co-operation the correction can be performed without anaesthesia and with the help of X-rays.

BRIEF DESCRIPTION OF THE FIGURES

The invention will be better understood by means of a preferred but non-exclusive embodiment of an orthopaedic device for out-patient use described and illustrated with reference to the appended table of drawings provided by way of non-limitative examples, in which.

DESCRIPTION OF A PREFERRED EMBODIMENT

Figure 1:
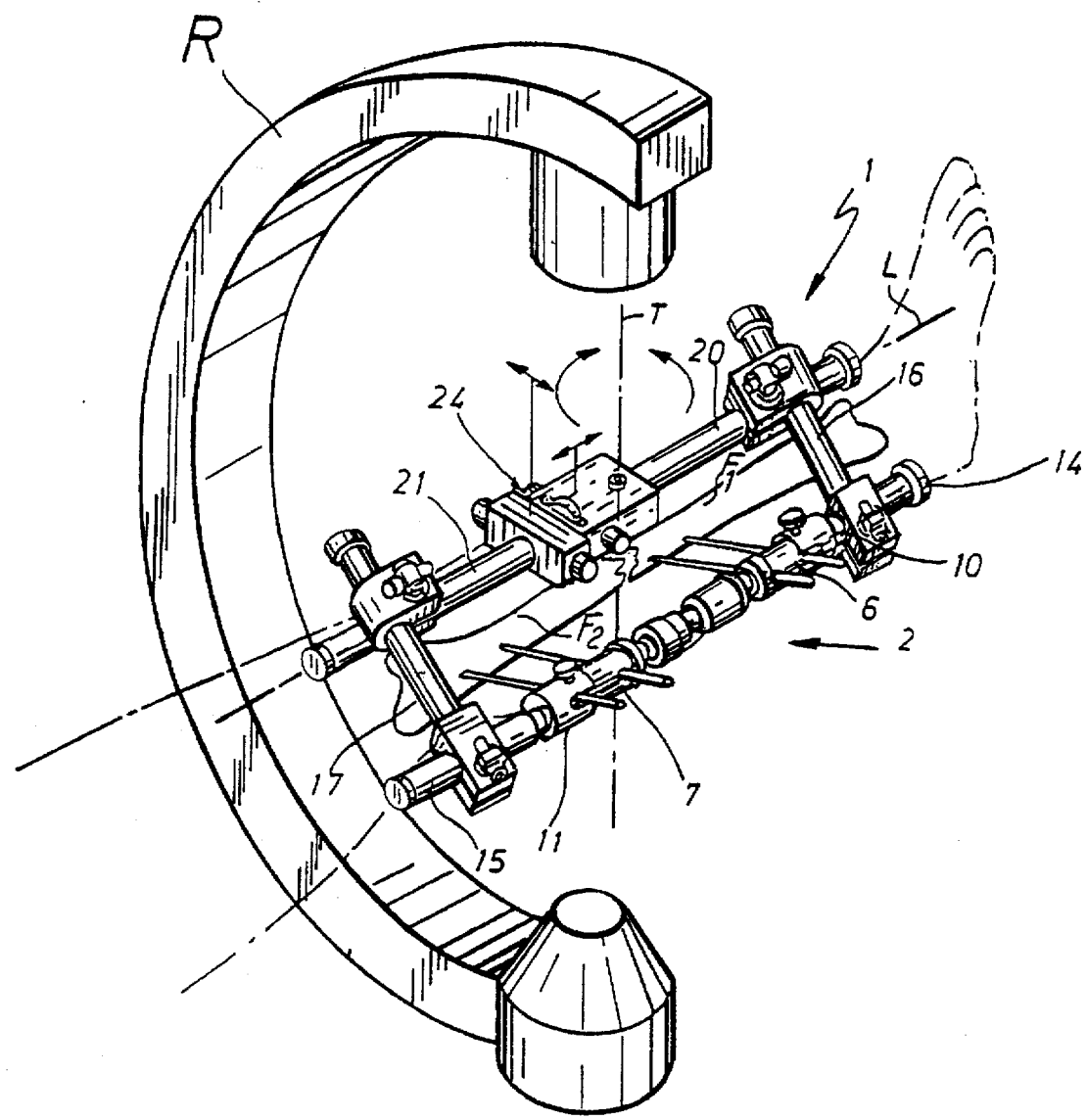
FIG. 1 shows a perspective view of a device according to the invention mounted on an external fixation unit anchored to a fractured limb and subjected to out-patient radioscopy.
Figure 2:
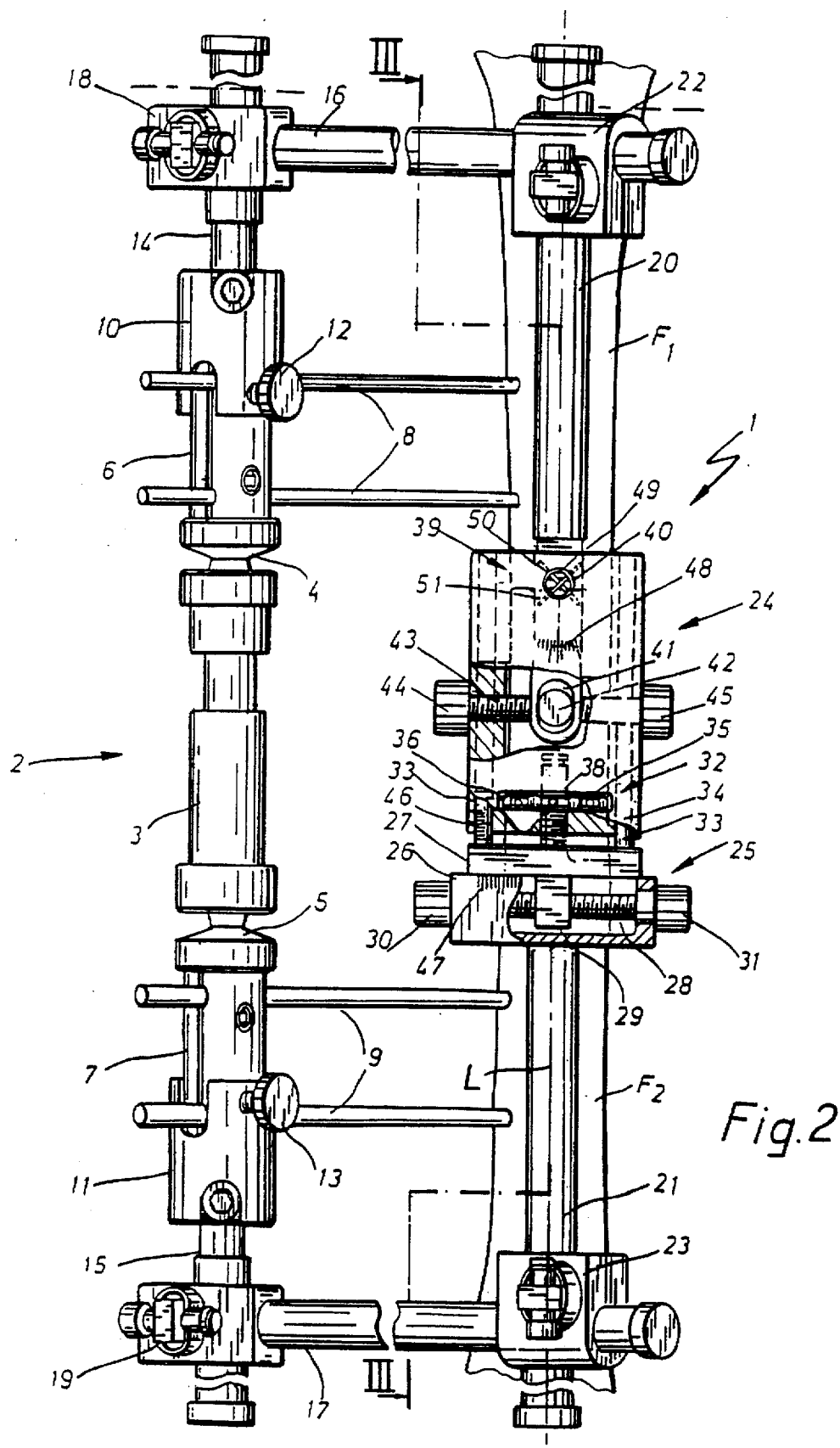
FIG. 2 shows a frontal view in partial cross-section of the device in FIG. 1.
Figure 3:
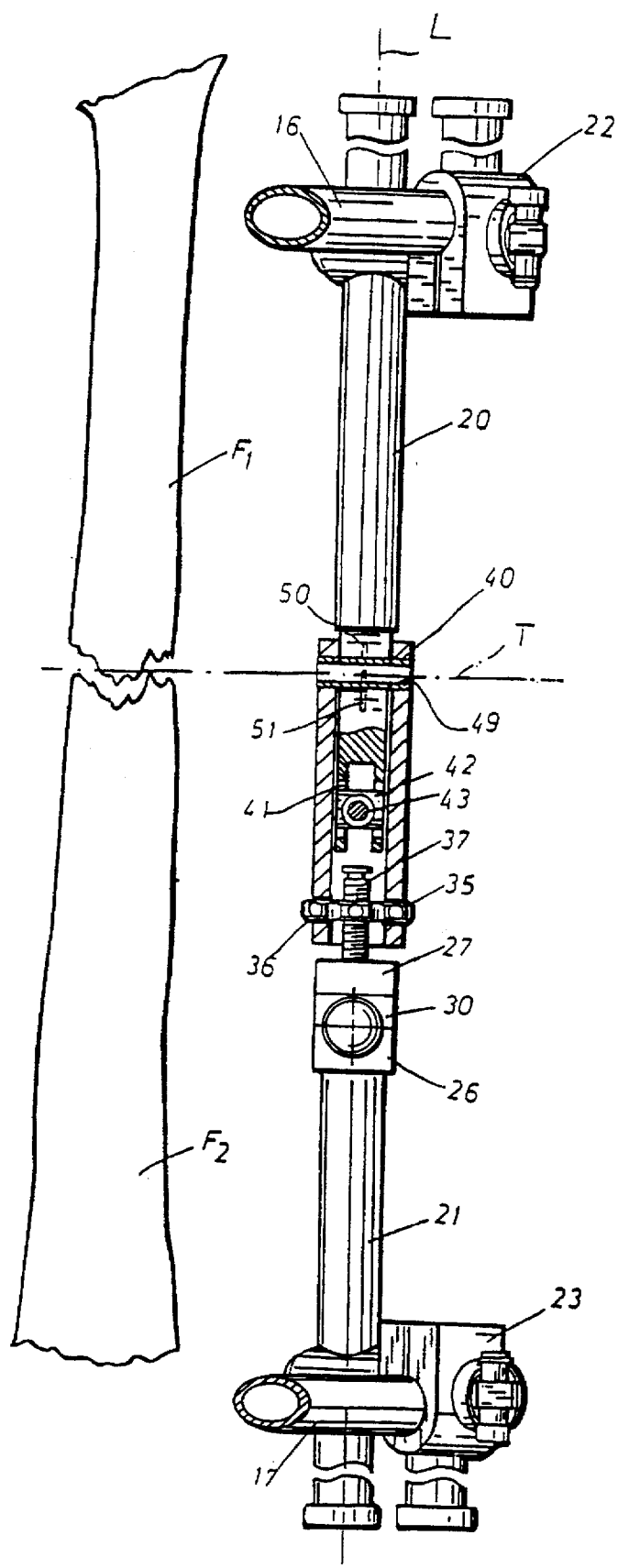
FIG. 3 shows a lateral view in partial cross-section of the device in FIG. 2.
Figure 4:
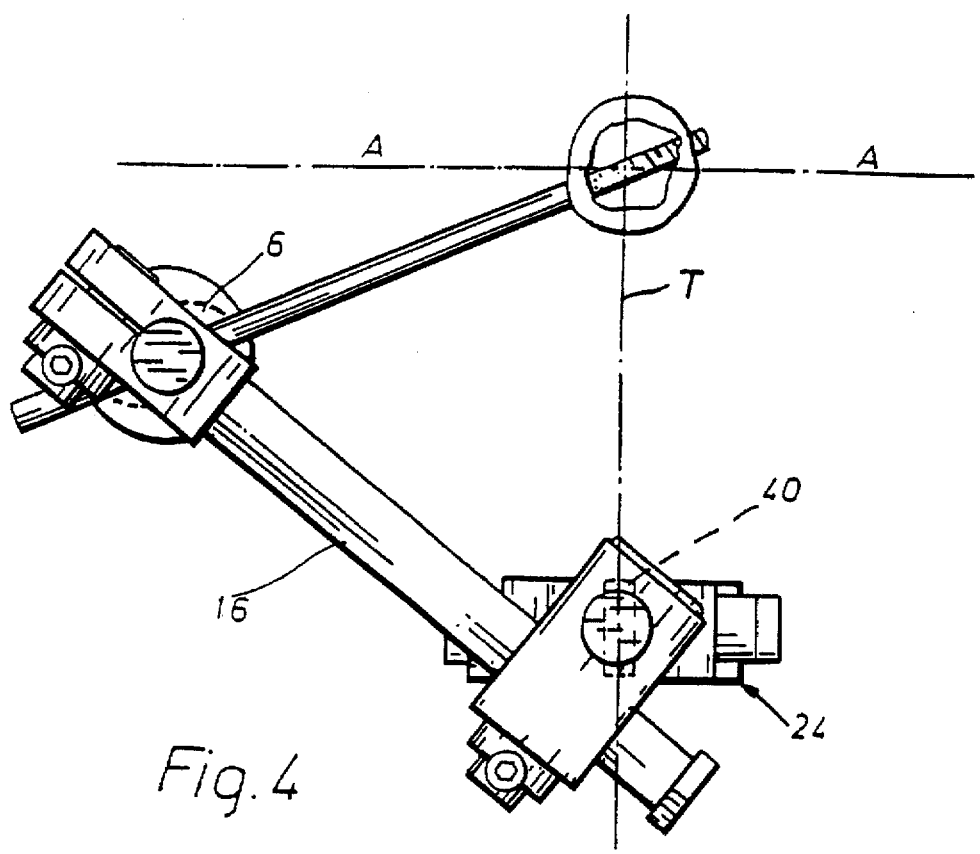
FIG. 4 shows an axial view of the device in FIG. 2 acting in a first axial plane A—A.
Figure 5:
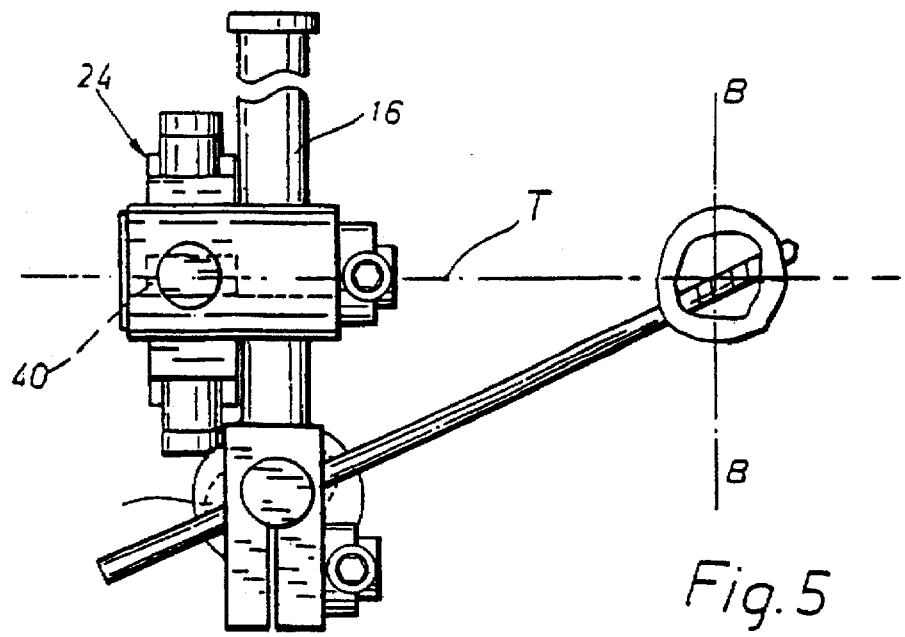
FIG. 5 shows an axial view of the device in FIG. 2 acting in a second axial plane B—B substantially perpendicular to plane A—A.
Figure 6:
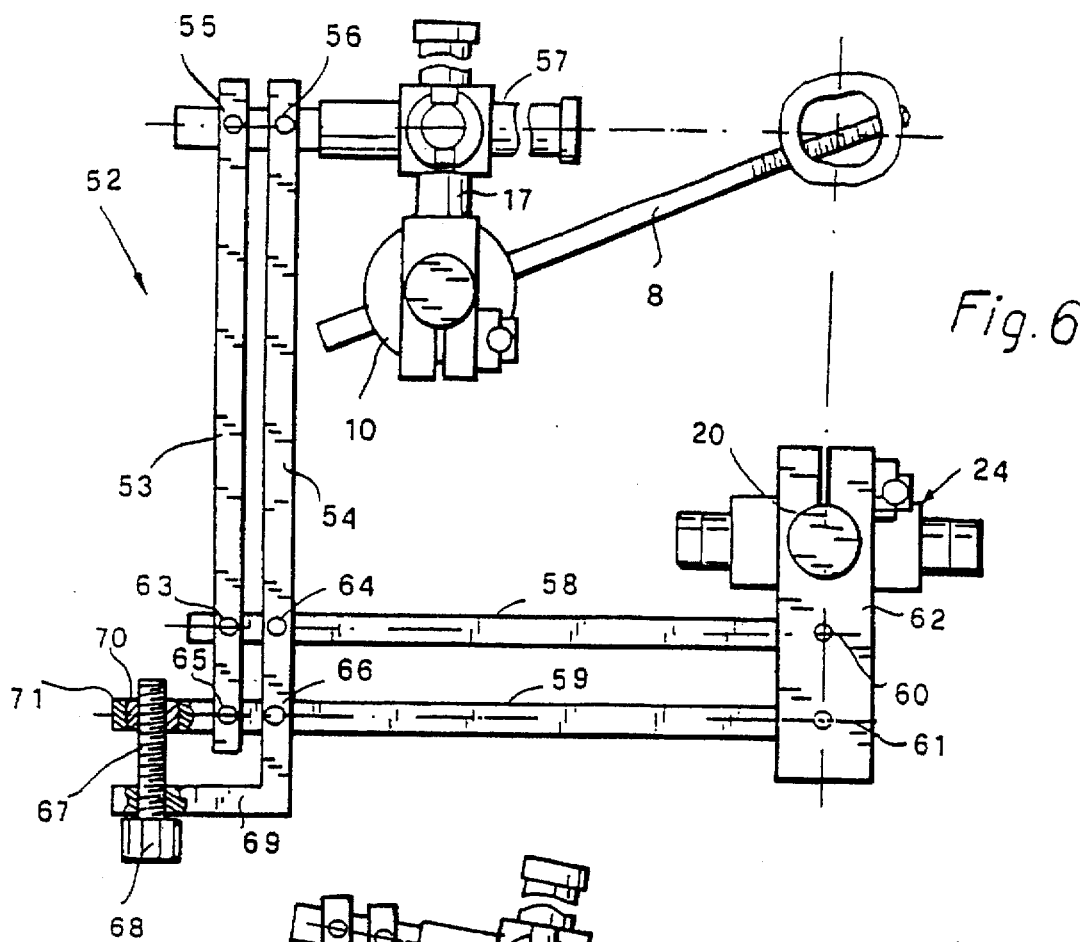
FIG. 6 shows an axial view of the device according to the invention provided with means for the correction of torsion.
Figure 7:
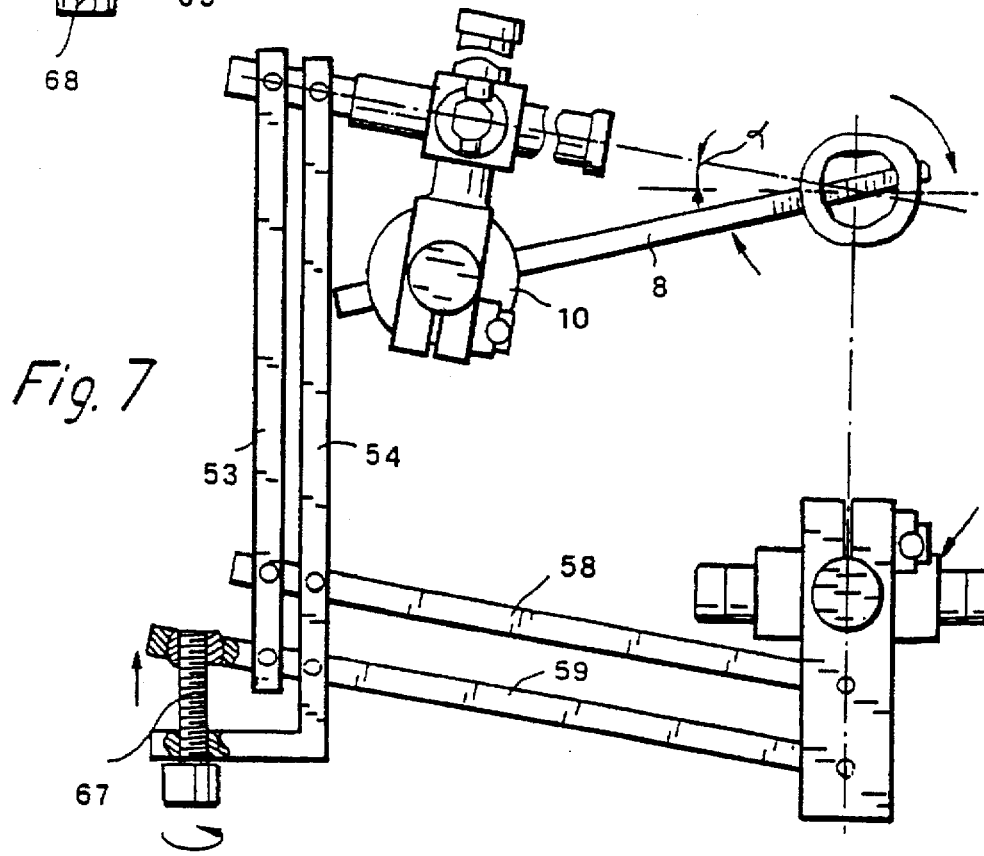
FIG. 7 shows an axial view of the device according to the invention with the device in FIG. 6 in an operating stage.

With reference to the figures mentioned, a device for the gradual correction of fractures on an out-patient basis, indicated as a whole by reference number 1, is suitable for use in combination with an axial fixation unit 2 of the type described, e.g. in patent U.S. Pat. No. Re 31,809 or in Italian patent application VR 92 A000070 in the name of ORTHOFIX.

In general fixation unit 2 comprises an elongatable central member 3 which joins corresponding end bolt-holding clamps 6, 7 by means of joints 4, 5. The latter clamps are fixed to corresponding pairs of bone bolts 8, 9 which are in turn inserted into fractured pieces F1, F2 upon operation in an operating theatre.

Device 1 according to the invention comprises a pair of end supports 10, 11, generally in the form of sockets with a central cavity which can house and then rigidly immobilise clamps 6, 7 of fixation unit 2 by means of securing bolts 12, 13.

Supports 10, 11 are coupled to a first pair of longitudinal bars 14, 15 by means of rigid coupling members. Longitudinal bars 14, 15 are connected to transverse bars 16, 17 respectively by means of joints 18, 19 of the stirrup type with lateral edges which can be brought together elastically by means of a tie rod activated by an eccentric pin.

In turn the pair of transverse bars 16, 17 is joined to a second pair of longitudinal bars 20, 21 by means of further stirrup joints 22, 23 which are similar to the above. Bars 20, 21 are normally aligned with an axis L which defines the longitudinal axis of the device.

The adjacent ends of longitudinal bars 20, 21 are joined to a central body 24 of approximately prismatic shape, by connection means which can be adjusted in the longitudinal, transverse and angular directions respectively, and which have structures and functions which will be described in detail hereinbelow.

Transverse adjustment is used to correct the displacement of supports 10, 11 in a plane passing through the longitudinal axis L of the device in order to remove any misalignment between the fractured pieces F1, F2 in a direction perpendicular to the axis of the fracture.

To this aim transverse adjustment means, indicated as a whole by reference number 25, are provided and comprise, on the one hand, a guide 26 which is integral with bar 21 and which extends perpendicular to axis L, and on the other hand by a slide 27 with a transverse cross-section which complements the guide, preferably by dovetailing, which is slidably engaged in guide 26. Translational movement of slide 27 in guide 26 is preferably effected by means of an operating device of the nut and bolt type, in which bolt 28 is rotatably supported by guide 26 and bolt 29 is integral with the lower part of slide 27. Bolt 28 may be conveniently rotated by terminal knobs 30, 31.

Adjustment in the longitudinal direction makes it possible to vary the longitudinal distance between supports 10, 11, i.e. to apply axial tension or compression to the fractured pieces F1 F2, bringing the separated edges together to a greater or lesser extent.

To this aim means are provided for longitudinal adjustment, indicated as a whole by reference number 32, which comprise longitudinal guide means formed from four smooth rods 33 which are fixed at one end to slide 27 and extend parallel to the axis of bar 21. Rods 33 are accurately and slidably housed in corresponding longitudinal seals 34 in central body 24, which itself comprises a second slide or carriage which moves perpendicularly with respect to the first guide means.

Longitudinal motion of body 24 with respect to slide 27 may be effected by means of an operating member also of the bolt and nut type, comprising a ring nut 35 housed in a slot 36 in central body 24 and with a central threaded hole in which a threaded rod 37 which has one end fixed to slide 27 is engaged.

Appropriately, the periphery of ring nut 35 is provided with projections so that it may be gripped, and radial holes 38 for the insertion of a pin or screwdriver.

Angular adjustment, which may apply to only one of longitudinal bars 20, 21, e.g. bar 20, serves to correct the relative inclination of supports 10, 11, and therefore of the broken pieces in a rotational plane defined by the lines of action of the transverse and longitudinal means of attachment.

Angular adjustment means, indicated as a whole by reference are provided for this purpose. These means comprise an end portion of bar 20 inserted into a cavity in body 24 and hinged thereto by means of a transverse pin 40 which constitutes the fulcrum for bar 20 with respect to central body 24. The axis of pin 40 is perpendicular to both the longitudinal axis of bar 20 and the plane defined by the lines of action of transverse 25 and longitudinal 32 adjustment means.

The inner end of bar 20 is fork shaped with eyelet holes 41 which slidably house a cylindrical sleeve 42. The latter has a through hole, perpendicular to its own axis and threaded internally, which is engaged by an externally threaded rod 43 which is rotatably mounted in main body 24. Knobs 44, 45 for convenient rotation of threaded rod 43 from the exterior are fixed to the ends of threaded rod 43 which project from body 24.

Suitable scales graduated in millimetres and degrees, indicated by 46, 47, 48 respectively, may be provided on adjustment means 25, 32 and 39 described above to provide micrometric control of the degree of transverse, longitudinal and angular adjustment for the connection means.

The device may be used with the help of a brilliance amplifier R, illustrated diagrammatically in FIG. 1. To reduce to a minimum undesired movements in the transverse and longitudinal directions, such as normally occur when setting is effected by means of splints and traditional devices, the axis Y of pin 40 which coincides with the fulcrum of angular adjustment means 39 is initially aligned with the centre of the fracture. For this purpose body 24 is constructed of a radio-transparent base material, such as e.g. methacrylate or polycarbonate, so that X-rays can pass through this component, while pin 40 is of a radio-opaque material such as steel or aluminium, in order that the axis of rotation of the angular adjustment means may be identified by contrast. Also pin 40 has a central hole 49 into which is inserted a pair of steel wires 50, 51, placed in planes at right angles to each other and intersecting the axis T of the pin 40. This device functions as an optical sighting device to allow the surgeon to centre the axis T of rotation on the centre of the fracture. To correct any twisting of the fractured pieces around the axis of the limb parallel to the longitudinal axis L of the device, torsion means, indicated as a whole by reference number 52, are provided and are used to impart a rotation about the axis of the limb to supports 10, 11 without producing any undesired movements in transverse directions.

In particular device 52 may comprise a first pair of parallel rods 53, 54, articulated at one end at 55, 56 to a transverse bar 57, coupled to transverse bar 16 which is in turn joined to support 10. A second pair of mutually parallel rods 58, 59 is articulated at one end at 60, 61 to a clamp 62 attached to longitudinal bar 20, which is in turn joined to central body 24. The two pairs of rods 53, 54 and 58, 59 lie in the same transverse plane, perpendicular to longitudinal axis L, and have second adjacent ends which are likewise connected at 63, 64, 65, 66 so as to form a deformable articulated parallelogram. A bolt 67 with an expanded knob head 68 can rotate at one end 69 of rod 54 which is bent through 90 degrees and has its free end engaged in a spherical bush 70 imprisoned in the end 71 of rod 59. Rotating bolt 67 deforms the articulated parallelogram described above bringing ends 69 and 71 of rods 54 and 59 closer together or further apart, and causing support 10 to rotate through an angle around the axis of the limb, without components in other transverse directions, effectively correcting any twisting of the broken pieces.

The device functions as follows:

The surgeon connects supports 10, 11 to clamps 6, 7 making sure to immobilise them rigidly by means of bolts 12, 13, but leaving stirrup joints 18, 19, 22, 23 slack. He then places the limb under the brilliance amplifier seeking a first plane A—A in which the transverse, longitudinal and angular displacements of the fracture can clearly be seen. This device may also be provided with a graduated scale, not illustrated in the drawings, for micrometric control of the amount of torsional correction.

After having positioned the device parallel to the axis of the limb as well as possible, and with central body 24 approximately parallel to plane A—A, the surgeon lines up axis T with the centre of the fracture, using pin 40 as a sight and X-rays.

He then immobilises joints 18, 19, 22, 23, slackens universal joints 4, 5 of fixation unit 2 and proceeds to make transverse, longitudinal, angular and if necessary torsional adjustments to the fracture, by acting on knobs 30, 31, ring nut 35, knobs 44, 45 and bolt 67 respectively, checking the magnitude of the corrections made by reading scales 46, 47, 48. Once the correction has been made the surgeon again immobilises universal joints 4, 5 of fixation unit 2.

Once correction has been performed in plane A—A, the surgeon can proceed to further correction in a second plane B—B perpendicular or transverse to the first, and in other planes other than the first plane so as to achieve optimum correction of the fracture in the shortest time possible and with a minimum use of X-rays.

The device according to the invention is susceptible of numerous modifications and variants all of which fall within the scope of the invention described in the appended claims. For example, externally controlled mechanical or electromechanical actuators may be used instead of manual control means of the nut and bolt type.

We claim:

1. An orthopaedic device and external fixation unit, in combination, for the gradual external correction of fractures which have already been set in the operating theatre, comprising an elongate structure defining a longitudinal axis which can be positioned parallel to a fractured limb, in which the structure has a pair of end supports releasably anchored to corresponding bolt-holding clamps of the external fixation unit adapted to being implanted onto fractured pieces, a central body connected to the supports by adjustable connection means which comprise longitudinal adjustment means to correct the longitudinal distance between the supports, transverse adjustment means to correct transverse offsets between the supports, angular adjustment means to correct the relative inclination of at least one of the supports with respect to the longitudinal axis by rotation about a lateral axis, and centering means to align the transverse axis with the centre of the fracture, in which the lateral axis is perpendicular to the plane of action of the longitudinal and transverse adjustment means, the central body comprising a block of radio-transparent material having a central cavity, the longitudinal and transverse adjustment means being located at one of the longitudinal ends of the body, and the angular adjustment means being located at the other longitudinal end.

2. The combination according to claim 1, in which the end supports have opposing cavities capable of housing the terminal portions of the clamps of the fixation unit and can be anchored to the terminal portions by means of releasable immobilizing means.

3. The combination according to claim 2, in which the connection means also comprise, for each support, a first longitudinal bar connected to a corresponding support and attached to a transverse bar, which is in turn joined to a second longitudinal bar coupled to a longitudinal extremity of the central body.

4. The combination according to claim 3, in which a device for gradually correcting any torsion existing between the fractured bones around the axis of the limb parallel to the longitudinal axis is mounted between at least one of the supports and the corresponding transverse bar.

5. The combination according to claim 4, in which the torsion device comprises an articulated system acting on a plane perpendicular to the longitudinal axis.

6. The combination according to claim 5, in which the articulated system comprises two pairs of transverse rods in two parallel pairs, having close ends which are joined together in such a way as to form an articulated parallelogram with distal ends connected to the corresponding transverse and longitudinal bars respectively.

7. The combination according to claim 6, in which the rod system comprises a bolt and nut type adjustment member acting between two opposing rods of the parallelogram in order to deform it and thus bring about rotation of the support integral with the transverse member about the axis of the limb.

8. The combination according to claim 2, in which the longitudinal bars and transverse bars (16; 17) placed on either side of the central body are connected together by means of tightenable stirrup joints.

9. The combination according to claim 1, in which the transverse adjustment means comprise a first slide coupled to the central body and retained slidably by first transverse guide means integral with one of the second longitudinal bars.

10. The combination according to claim 9, in which the transverse adjustment means also comprise a first operating member of adjustable fasteners acting on the first slide to move it in a micrometric fashion along the transverse guide means.

11. The combination according to claim 7, in which the longitudinal adjustment means comprise a second slide associated with the main body which can slide along longitudinal guide means integral with the first slide.

12. The combination according to claim 11 in which the longitudinal adjustment means also comprise a second operating means of adjustable fasteners acting on the second slide to cause it to move along the longitudinal guide means.

13. The combination according claim 1, in which the angular adjustment means comprise a pin inserted into the block of radio-transparent material, one of the second longitudinal bars being hinged upon the pin having a fulcrum on the pin at a particular distance from its free end which is inserted into the central cavity of the body.

14. The combination according to claim 13, in which the angular adjustment means also comprise a bolt and nut operating means acting on the free end of the bar inserted into the internal cavity of the body.

15. The combination according to claim 14 in which the pin has a central through hole with a pair of wires which are at right angles to each other and are radio-opaque, forming the centering means.

\* \* \* \* \*